United States Patent [19]

Pitt et al.

[11] 4,096,251
[45] Jun. 20, 1978

[54] DIETHYL 2-PYRIDINE THIONOPHOSPHONATE AS AN INSECTICIDE ACTIVATOR

[75] Inventors: Leland S. Pitt, San Jose; George B. Large, Orinda; Alan MacDonald, Albany, all of Calif.

[73] Assignee: Stauffer Chemical Company, Westport, Conn.

[21] Appl. No.: 719,033

[22] Filed: Aug. 30, 1976

[51] Int. Cl.² .................. A01N 9/36; C07D 213/04
[52] U.S. Cl. ......................... 424/200; 260/294.8 K
[58] Field of Search ............. 260/294.8 K, 297 P; 424/200

[56] References Cited

U.S. PATENT DOCUMENTS

| | | | |
|---|---|---|---|
| 3,621,021 | 11/1971 | Miller et al. | 260/250 |
| 3,665,001 | 5/1972 | Valint | 260/239 A |
| 3,673,196 | 6/1972 | Redmore | 260/294.9 |
| 3,821,232 | 6/1974 | Redmore | 260/294.8 K |

OTHER PUBLICATIONS

Frear — Pesticide Index, 1969, p. 194.

*Primary Examiner*—Leonard Schenkman
*Attorney, Agent, or Firm*—Joel G. Ackerman

[57] ABSTRACT

The novel compound diethyl 2-pyridine thionophosphonate

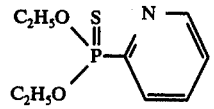

has been found to possess insecticidal activation properties when combined with the known insecticide N-(mercaptomethyl) phthalimide S-(O,O-dimethyl phosphorodithioate).

9 Claims, No Drawings

DIETHYL 2-PYRIDINE THIONOPHOSPHONATE AS AN INSECTICIDE ACTIVATOR

DESCRIPTION OF THE INVENTION

This invention relates to the novel compound diethyl 2-pyridine thionophosphonate, and to its properties as an activator for the insecticide N-(mercaptomethyl)phthalimide S-(O,O-dimethyl phosphorodithioate), a commercial insecticide sold under the trademark "Imidan" ®.

SUMMARY OF THE INVENTION

In one aspect this invention comprises the novel compound diethyl 2-pyridine thionophosphonate.

In another aspect this invention comprises an insecticidal composition of matter comprising N-(mercaptomethyl)phthalimide S-(O,O-dimethyl phosphorodithioate) and an activating amount of diethyl 2-pyridine thionophosphonate.

In a further aspect this invention comprises a method of controlling insects comprising applying to the insect or the habitat thereof an insecticidally effective amount of a composition comprising N-(mercaptomethyl)phthalimide S-(O-O-dimethyl phosphorodithioate) and an activating amount of diethyl 2-pyridine thionophosphonate.

The diethyl 2-pyridine thionophosphonate was prepared in the following manner:

In a 500 ml. flask were placed 250 ml. dry tetrahydrofuran and 16.8 g. (0.150 mole) potassium tert.-butoxide. Then 23.1 g. (0.150 mole) diethyl hydrogen thionophosphonate was added dropwise with the temperature maintained below 30° C. There was then added dropwise 37.4 g. (0.150 mole) N-ethoxypyridinium ethosulfate with stirring at 5° to 10° C, with cooling in an ice bath. When the salt addition was complete the mixture was allowed to warm to room temperature and was stirred for about 2 hours. There were then added 75 ml. water, 25 ml. of a saturated sodium chloride solution and 100 ml. of chloroform. The mixture was allowed to separate into aqueous and organic phases. The organic phase was washed with a saturated aqueous sodium chloride solution, dried over magnesium sulfate and stripped of solvent.

There was obtained 27.5 g. (79% of theoretical), of a red-brown liquid, $n_D^{30}$ 1.4967, which was confirmed by IR (infa-red) and NMR (nuclear magnetic resonance) spectral analyses to be the desired compound.

The N-ethoxypyridinium ethosulfate used in the above procedure was prepared by reacting 59.2 g. (0.623 mole) pyridine N-oxide with 95.8 g. (0.623 mole) ethyl sulfate, with warming. After the exothermic reaction was complete, the mixture was heated at 80°–90° C. for 2 hours and cooled. A thick red oil, $n_D^{30}$ 1.4990 was obtained, which was confirmed by IR and NMR analyses to be the desired compound.

Insecticide Evaluation

Tests were conducted on three insects, namely the Saltmarsh Caterpillar, [*Estigmene acrea* (Drury)]; the Tobacco Budworm, [*Heliothis virescens* (F.)]; and the Cabbage Looper, [*Trichoplusia ni* (Hübner)]. The following procedures were employed.

Saltmarsh Caterpillar [*Estigmene acrea* (Druryl)], (SMC in Table 1): Test solutions containing both N-(mercaptomethyl) phthalimide S-(O,O-dimethyl phosphorodithioate) and diethyl 2-pyridine thionophosphonate were prepared using acetone and water (50/50) as a solvent. The then prepared solutions were mixed to produce a series of mixtures in which the ratio (by weight) of the insecticide to the activator compound (diethyl 2-pyridine thionophosphonate) ranged from 1:0.1 to 1:10. Sections of curly dock (Rumex crispus) leaves, approximately 1 × 1.5 inches, were immersed in the test solutions for 2-3 seconds and placed on a wire screen to dry. The dried leaves were placed in Petri dishes containing a moistened piece of filter paper and infested with 5 second-instar saltmarsh caterpillar larvae. Mortality of the larvae was recorded 48 hours later, and a piece of synthetic media was added to dishes containing survivors. These were then held for five additional days to observe for any delayed effects of the test compounds.

Test concentrations of the toxicant (mixture) ranged from 0.5% down to that at which approximately 50% mortality occurred.

Tobacco Budworm [Heliothis virescens (F.)], (TBW in table 1):

(a) similarly, tests were conducted using sections of Romaine lettuce (*Latuca sativa*) leaves, infested with 5 second-instar tobacco budworm larvae. Test concentrations ranged from 0.1% of the toxicant mixture down to that at which approximately 50% mortality occurred.

(b) (topical assay) ("TBW - top" in Table 1) The test compound or mixtures were diluted in acetone and topically applied in 1- to 5- $\mu l$ drops to the anterior dorsal surface of third-to-fourth-instar tobacco budworm larvae. The treated larvae were placed in groups of five in Petri dishes containing synthetic media. Moratality was determined two days later. Test doses generally ranged from 1000 ug. toxicant/$\mu g$. larval weight down to that at which approximately 50% mortality occurred.

Cabbage Looper [*Trichoplusia ni* (Hübner)], (CL in Table 1): Similarly to the Saltmarsh Caterpillar, tests were conducted using cotyledons of hyzini squash (*Calabacita abobrinha*) infested with 5 second-instar cabbage looper larvae. Test concentrations ranged from 0.1% of the toxicant down to that at which approximately 50% mortality occurred.

In all three tests, controls were run identically to the tests described, with the exception that in one control only N-(mercaptomethyl)phthalimide S-(O,O-dimethyl phosphorodithioate) was used and in another control only diethyl 2-pyridine thionophosphonate was used.

The following Table 1 contains results of the various tests described above. The term "insecticide" refers to N-(mercaptomethyl)phthalimide S-(O,O-dimethyl phosphorodithioate) and the term "activator" refers to diethyl 2-pyridine thionophosphonate.

Table 1

| Test Composition | SMC $LD_{50}$ % | A.F. | TBW $LD_{50}$ % | A.F. | TBW-top. $LD_{50}$ $\mu g/g$ | A.F. | CL $LD_{50}$ % | A.F. |
|---|---|---|---|---|---|---|---|---|
| insecticide | > 0.1 | | > 0.1 | | > 1000 | | 0.02 | |
| activator | > 0.2 | | > 0.2 | | > 5000 | | > 0.2 | |
| insecticide: | | | | | | | | |

Table 1-continued

| Test Composition | SMC LD$_{50}$ % | SMC A.F. | TBW LD$_{50}$ % | TBW A.F. | TBW-top. LD$_{50}$ μg/g | TBW-top. A.F. | CL LD$_{50}$ % | CL A.F. |
|---|---|---|---|---|---|---|---|---|
| activator, 1:10 insecticide: | 0.01 | > 1.6 | 0.01 | > 1.6 | — | — | 0.008 | > 1.25 |
| activator, 1:5 insecticide: | 0.02 | > 1.4 | 0.02 | > 1.4 | 30 | > 16.6 | 0.02 | — |
| activator, 1:1 insecticide: | 0.02 | > 3.3 | 0.03 | > 2.2 | 100 | > 8.3 | 0.03 | — |
| activator, 1:0.5 insecticide: | > 0.1 | — | 0.03 | > 2.6 | — | — | 0.03 | — |
| activator, 1:0.1 | > 0.1 | — | 0.1 | — | — | — | 0.03 | — |

The Activating Factor (A.F.) is arrived at by using the following formula from the expected response for a given combination of two insecticides:

$$A.F. = \frac{LD_{50} \text{ of insecticide } \frac{1}{(XY + 1)}}{\text{Experimental } LD_{50} \text{ of combination}}$$

in which $X$ equals the ratio of the percent or rate of the activator to the percent or rate of the insecticide and $Y$ equals the ratio of the $LD_{50}$ of the insecticide to the $LD_{50}$ (highest value tested) of the activator. The experimental $LD_{50}$ of the combination is in terms of the insecticide only.

The A. F. is therefore the ratio of the expected $LD_{50}$ of the combination divided by the experimental $LD_{50}$. It is noted that when the observed response is greater than the expected response, the A.F. is greater than 1.

Thus, from the forgoing data, the novel compound diethyl 2-pyridine thionophosphonate is shown to be an effective activator or synergist for the insecticie N-(mercaptomethyl) phthalimide S-(O,O-dimethyl phosphorodithioate) against insects, particularly against lepidoptera, and more specifically against insects of the genera Estigmene, Heliothis and Trichoplusia. With respect to the saltmarsh caterpillar, activity is demonstrated at weight ratios of insecticide: activator of 1:1 to 1:10; with respect to the tobacco budworm, activity is dimonstrated at weight ratios of insecticide: activator of 1:10 to 1:0.5. In both cases, neither the insecticide nor the activator, alone, was found to be effective against either insect.

Thus, the compositions of the present invention can also be considered to be synergistic insecticidal compositions in that neither compound was shown to be active, individually, against the particular insect involved.

Against the cabbage looper, the insecticide showed some activity, but this activity was enhanced by mixing the insecticide with 10 times its weight of the activator. With such activity shown, it would be expected that activation would also exist against the insect at higher weight ratio of activator; insecticide. Such would also be the case with the other insects for which test results are included hereon.

What is claimed is:

1. A compound having the formula

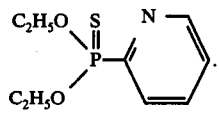

2. An insecticidal composition comprising N-(mercaptomethyl)phthalimide S-(O,O-dimethyl phosphorodithioate) and an activating amount of

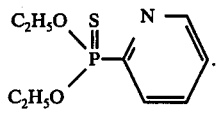

3. A process of controlling insects applying to the insects or the habitat thereof an insecticidally effective amount of a composition comprising N-(mercaptomethyl)phthalimide S-(O,O-dimethyl phosphorodithioate) and an activating amount of

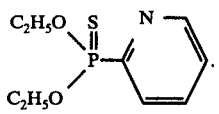

4. A process according to claim 3 in which the insect to be controlled is an insect of the genus Estigmene.

5. A process according to claim 3 in which the weight rato of N-(mercaptomethyl)phthalimide S-(O,O-dimethyl phosphorodithioate) to diethyl 2-pyridine thionophosphonate is between about 1:1 and 1:10.

6. A process according to claim 5 in which the insect to be controlled is *Estigmene acrea*.

7. A process according to claim 3 in which the insect to be controlled is an insect of the genus Heliothis.

8. A process according to claim 7 in which the weight ratio of N-(mercaptomethyl) phthalimide S-(O,O-dimethyl phosphorodithioate) to diethyl 2-pyridine thionophosphonate is between about 1:0.5 and about 1:10.

9. A process according to claim 7 in which the insect to be controlled is *Heliothis virescens*.

* * * * *